(12) United States Patent
Wood

(10) Patent No.: US 6,418,802 B1
(45) Date of Patent: *Jul. 16, 2002

(54) PARTICLE SIZING APPARATUS AND METHOD OF USE THEREOF

(76) Inventor: Michael Anthony Wood, c/o Microbial Systems Ltd., The Viscount Centre, University of Warwick Science Park, Milburn Hill Rd., Coventry CV4 7HS (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/004,909

(22) Filed: Jan. 9, 1998

Related U.S. Application Data

(62) Division of application No. 08/754,823, filed on Nov. 21, 1996.

(51) Int. Cl.[7] ............................................... G01N 15/00
(52) U.S. Cl. ..................................... 73/865.5; 324/71.4
(58) Field of Search ....................... 73/865.5; 324/71.1, 324/71.4

(56) References Cited

U.S. PATENT DOCUMENTS

| | | | |
|---|---|---|---|
| 3,444,463 A | | 5/1969 | Coulter et al. |
| 3,739,258 A | | 6/1973 | Karuhn et al. |
| 3,868,498 A | | 2/1975 | Guggenbühl |
| 3,930,736 A | | 1/1976 | Coulter |
| 4,014,611 A | * | 3/1977 | Simpson et al. ............ 324/71.4 |
| 4,078,211 A | | 3/1978 | Longman, Jr. |
| 4,361,803 A | * | 11/1982 | Hogg ........................ 324/71.4 |
| 4,412,175 A | | 10/1983 | Maynarez |
| 4,450,435 A | | 5/1984 | James |
| 4,491,786 A | | 1/1985 | Godin |
| 4,600,880 A | | 7/1986 | Doutre et al. |
| 4,760,328 A | * | 7/1988 | Groves ....................... 324/71.4 |
| 4,835,457 A | * | 5/1989 | Hanss et al. ................ 324/71.4 |
| 4,977,517 A | | 12/1990 | Gibbs, Jr. et al. |
| 5,007,297 A | * | 4/1991 | Sommer ..................... 73/865.5 |
| 5,150,037 A | * | 9/1992 | Kouzuki .................... 324/71.4 |
| 5,905,214 A | * | 5/1999 | Inami ........................ 73/865.5 |
| 5,983,735 A | * | 11/1999 | Von Behrens et al. ....... 3/865.5 |

FOREIGN PATENT DOCUMENTS

| | | | |
|---|---|---|---|
| EP | 0 193 394 | * | 2/1985 |
| EP | 0 279 000 | * | 2/1987 |
| EP | 0 682 241 A1 | * | 5/1995 |

(List continued on next page.)

OTHER PUBLICATIONS

EPO Search Report dated Apr. 16, 1999 regarding European application EP97309373.5 (publication No. 0844475).
Search Reports (GB 97246110.0) dated Mar. 17, 1997 and Jul. 30, 1998.*

Primary Examiner—Hezron Williams
Assistant Examiner—Nashmiya Fayyaz
(74) Attorney, Agent, or Firm—Banner & Witcoff, Ltd.

(57) ABSTRACT

Apparatus for determining the size of a particle or cell within a fluid, includes a sample chamber for the fluid, a flow restrictor including an orifice, a pair of electrodes disposed on opposite sides of the orifice and signal measurer for measuring a signal representative of the impedance variation between the electrodes thereby to determine the size of a particle within the fluid passing through the orifice, and further including blockage detector for detecting blockage of the orifice, whether partial or complete. Apparatus for determining the size of particles or cells within a fluid, includes a sample chamber for the fluid, a flow restrictor including an orifice, a pair of electrodes disposed on opposite sides of the orifice and signal measurer for measuring a signal representing the impedance variation between the electrode thereby to determine the size of a cell within the fluid passing through the orifice, and further including an orifice deblocker for deblocking the orifice by causing movement of a particle at least momentarily held within the orifice.

17 Claims, 8 Drawing Sheets

FOREIGN PATENT DOCUMENTS

| | | | |
|---|---|---|---|
| GB | 722418 | * | 2/1955 |
| GB | 1061776 | * | 3/1967 |
| GB | 1121550 | * | 7/1968 |
| GB | 1160130 | * | 7/1969 |
| GB | 1254891 | * | 11/1971 |
| GB | 1268790 | * | 3/1972 |
| GB | 1271708 | * | 4/1972 |
| GB | 1331369 | * | 9/1973 |
| GB | 1359813 | * | 7/1974 |
| GB | 1371432 |   | 10/1974 |
| GB | 1448734 | * | 9/1976 |
| GB | 1459869 | * | 12/1976 |
| GB | 1463110 | * | 2/1977 |
| GB | 1539106 | * | 1/1978 |
| GB | 1521300 | * | 8/1978 |
| GB | 2 065 311 A | * | 6/1981 |
| GB | 1597904 | * | 9/1981 |
| GB | 2 096 768 A | * | 10/1982 |
| GB | 2 163 555 A | * | 8/1984 |
| GB | 2 319 618 A | * | 11/1996 |
| WO | WO 85/01108 | | 3/1985 |
| WO | WO 88/02486 | | 4/1988 |
| WO | WO 92/01934 | | 2/1992 |

\* cited by examiner

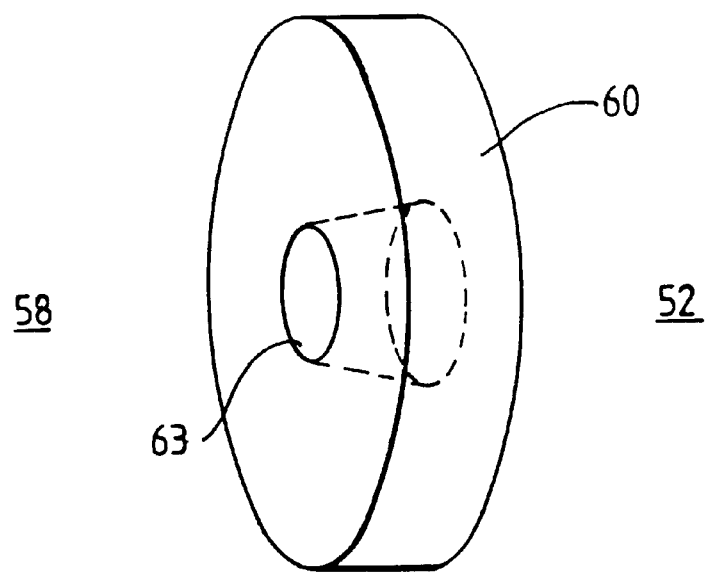
FIG.8.
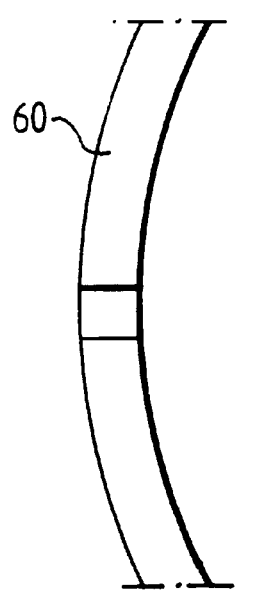 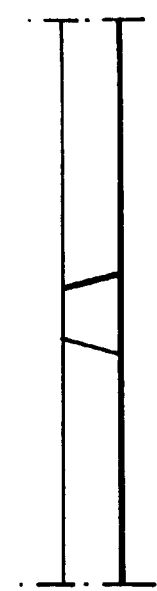 
FIG.9(a)  FIG.9(b)  FIG.9(c)

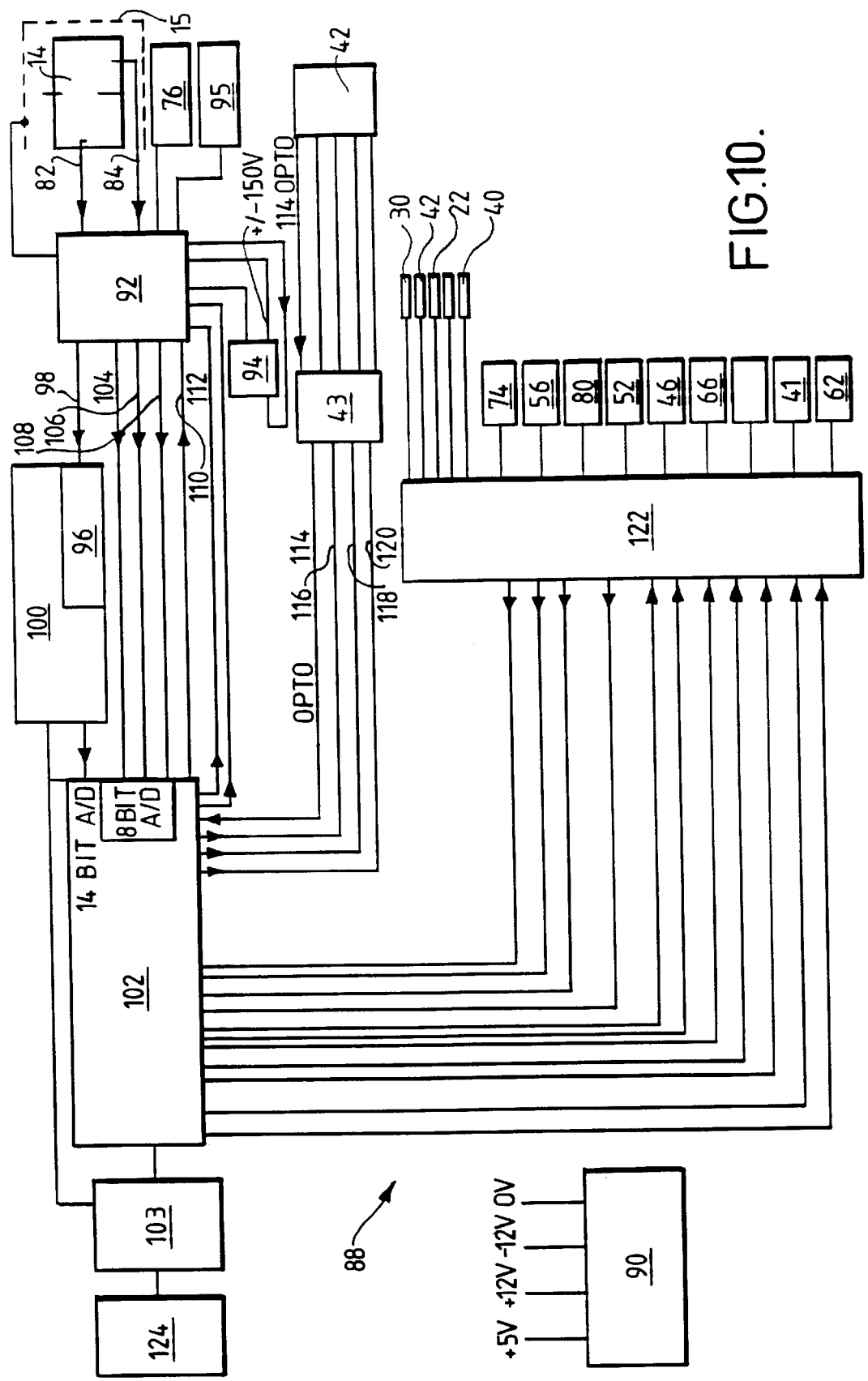

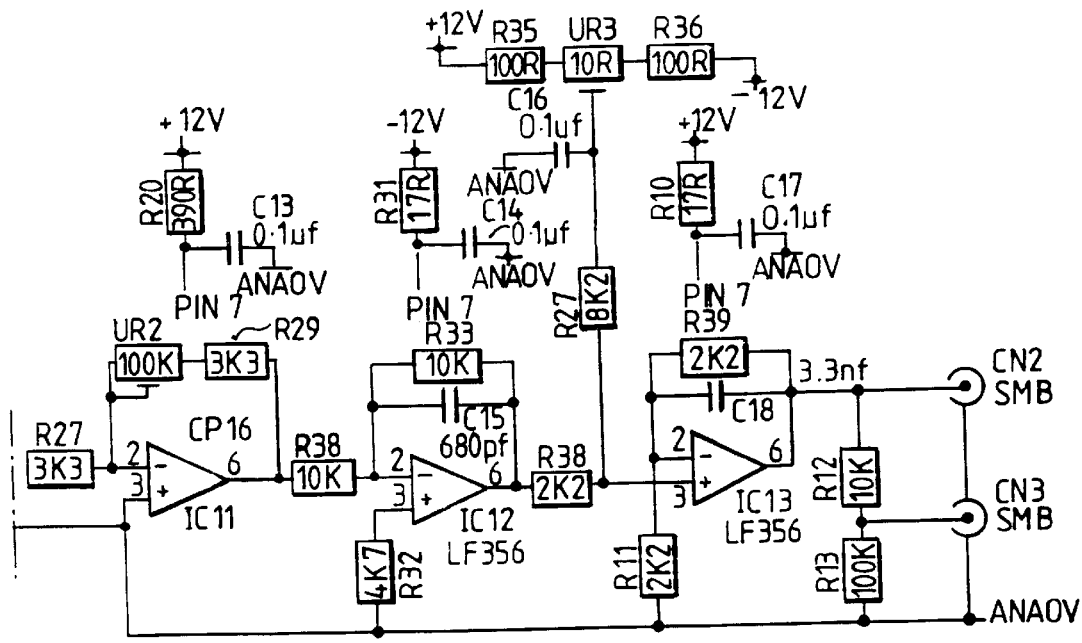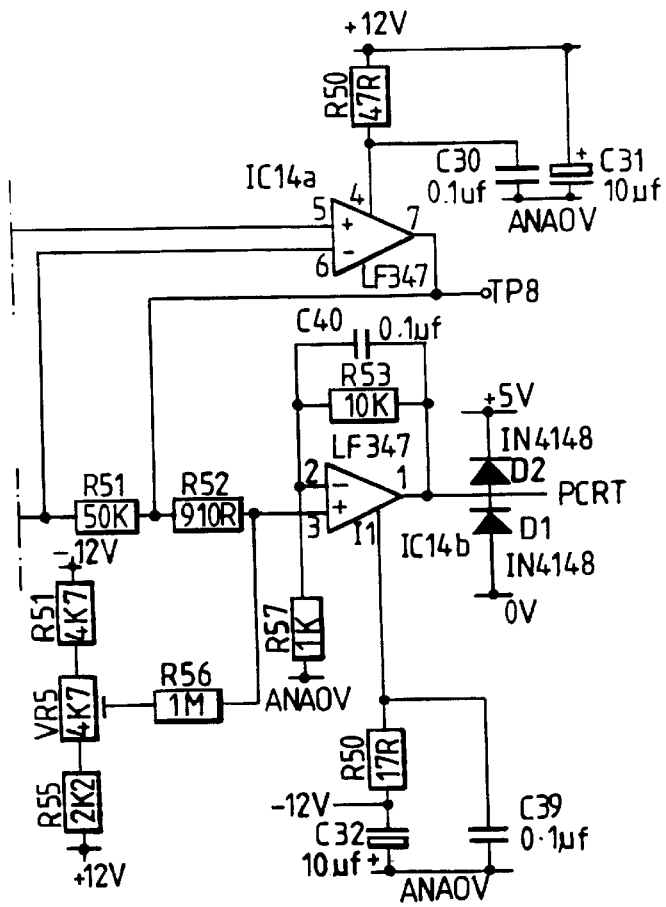
FIG.11b.

PARTICLE SIZING APPARATUS AND METHOD OF USE THEREOF

This application is a Divisional of U.S. application Ser. No. 08/754,823 filed Nov. 21, 1996 still pending.

FIELD OF THE INVENTION

The invention relates to particle or cell sizing and counting apparatus and to methods of operation thereof. In particular, the invention relates to apparatus which uses a technique of measuring the impedance at an orifice to determine the volume of a particle passing through the orifice.

BACKGROUND OF THE INVENTION

It is known from EP 0162607 to determine the size of a particle from the variation in impedance between a pair of electrodes in an electrolyte due to particle flow through an orifice in a flow restrictor disposed between the electrodes. An inherent problem of this type of system however, is that partial or complete blockage of the orifice can occur during measurements which requires that the flow restrictor comprising the orifice must be removed in order to be cleaned to allow further measurements. Additionally, if only partial blockage occurs the observed distribution of particle sizes in a sample will be affected due to prevention of flow by the blockage of larger particles through the orifice. This problem is particularly prevalent if one wishes to use a small orifice diameter of say five times the average particle size to enable good accuracy of particle sizing results.

SUMMARY OF THE INVENTION

The invention seeks to avoid or at least mitigate problems of the prior art including providing apparatus which detects blockage and or deblocks the orifice especially in the event of partial or complete blockage.

According to first aspect of the invention there is provided apparatus for determining the size of a particle or cell within a fluid, comprising a sample chamber for the fluid, a flow restrictor comprising an orifice, a pair of electrodes disposed on opposite sides of the orifice and means for measuring a signal representative of the impedance variation between the electrodes thereby to determine the size of a particle within the fluid passing through the orifice, and further comprising means for detecting blockage of the orifice, whether partial or complete. Beneficially the detection of a partial or complete blockage alerts the user to data corruption.

Preferably, the detecting means comprises means for monitoring the signal, which means detects occurrence of a predetermined variation of the signal indicative of blockage of the orifice. For example, particle passage through the orifice causes a signal pulse which is measured by the measuring means and wherein the monitoring means determines a width of the signal pulse and compares this width with a predetermined value thereby to detect partial or complete blockage of the orifice. The predetermined pulse width value can be determined from an average of previously measured pulse widths.

In another form, the monitoring means monitors the mean base line value of the signal to determine if a significant drift in mean base line value occurs which is indicative of partial or complete blockage of the orifice.

Alternatively or as well, the monitoring means compares the height of an individual signal pulse with a known value corresponding to a particle size in the order of or greater than a predetermined size such as the diameter of the orifice. Also, the monitoring means can comprise a saturation pulse or square wave detector. The square wave detector can compare the time for a pulse signal to pass through a first and second predetermined value and then return back through the predetermined first and second values. The square wave detector can be arranged to detect a characteristic recovery curve indicative of saturation of the measuring means.

In another form, the monitoring means measures the rate of occurrence of signal pulses and compares this rate with a predetermined rate. Also, the monitoring means can compare the number of detected signal pulses in a given time interval with a predetermined value, such as an average of previous measurements.

Beneficially, the monitoring means can analyse the background noise of the signal for predetermined variation, such as amplitude variation within a frequency range.

Further, the detecting means can comprise an orifice current detector for determining electrical current flow between the electrodes thereby enabling the monitoring means to compare orifice current with predetermined values. The detecting means can compare the orifice current value before or after measuring a signal or the mean of the two with an initial value measured before the signal measurement. The detecting means can determine if the difference is greater than a 10% increase or a 5% decrease, or if the difference is greater than 20% say.

Preferably, the measuring means comprises a 14 bit detector, or an analogue to digital converter having 14 bit resolution. Also, the apparatus preferably comprises means for applying a calibration signal to one of the electrodes and the monitoring means the signal across both electrodes, the monitoring means being adapted to compare the detected calibration signal with a pre-determined signal. The calibration signal can comprise a series of pulses. The calibration signal can be repeated a predetermined number of times to attempt to obtain an acceptable result with the predetermined signal, before providing an alarm to the user. Also, means for deblokcling the orifice by removing a particle at least momentarily held within the orifice can be provided.

According to another aspect of the invention there is provided apparatus for determining the size of a particle or cell within a fluid, comprising a sample chamber for the fluid, a flow restrictor comprising an orifice, a pair of electrodes disposed on opposite sides of the orifice and means for measuring a signal representative of the impedance variation between the electrodes thereby to determine the size of a particle within the fluid passing through the orifice, and further comprising means for deblocking the orifice by causing movement of a particle held at least momentarily within the orifice. Beneficially the deblocking means can effect in situ removal of the blockage, therefore, the apparatus allows continuous sampling without requiring the user to dismantle the sample chamber or remove the flow restrictor for cleaning when a blockage occurs.

Preferably, the deblocking means operably creates ultrasonic vibrations in the fluid in the region of the orifice. A series of electrical pulses can be applied to one of the pair of electrodes. The pulse frequency is preferably greater than 15 kHz, and preferably up to about 20 kHz. Beneficially, the flow restrictor can comprise material that exhibit the piezoelectric effect, thus to enhance the deblocking effect in the presence of electrical pulses.

Also, the deblocking means can comprise fluid propulsion means for effecting fluid flow at the flow restrictor. Preferably, the fluid propulsion means directs fluid substantially in the reverse direction to fluid flow during signal measurements.

Beneficially, means within the chamber can be used for directing fluid from the fluid propulsion means towards the flow restrictor. For example, a tapered region of the chamber can be used.

Another aspect of the invention provides a sample chamber housing for particle sizing apparatus comprising a pair of recesses each adapted to receive an electrode, an electrode in each recess, and a two-part sealant and adhesive for the electrodes. The adhesive can comprise a structural acrylic adhesive. The sealant can comprise a silicone based sealant such as RTV silicon rubber. The recess is preferably defined in a body of a polymer such as acrylic.

A further aspect of the invention provides a flow restrictor for particle sizing apparatus, comprising an orifice allowing flow of particles therethrough which orifice is tapered. The taper is preferably in the order of 5 to 30% of the mean orifice diameter.

A further aspect of the invention provides a flow restrictor wherein the material defining the orifice is flexible.

A yet further aspect of the invention provides use of a 14 bit analogue to digital converter in particle sizing apparatus.

BRIEF DESCRIPTION OF THE DRAWINGS

Embodiments of the invention will now be described by way of example only, with reference to the accompanying drawings in which;

FIG. 8 is a schematic perspective view of a second flow restrictor according to the invention;

FIGS. 9a, b and c are is a schematic side views of the restrictor of FIG. 8 in three different modes of use.

FIG. 10 is a schematic block diagram of part of the electronic control system for the apparatus according to the invention;

FIGS. 11A and 11B comprise a circuit diagram for part of the amplification circuit for the apparatus according to the invention.

DETAILED DESCRIPTION OF THE INVENTION

Figure 1:
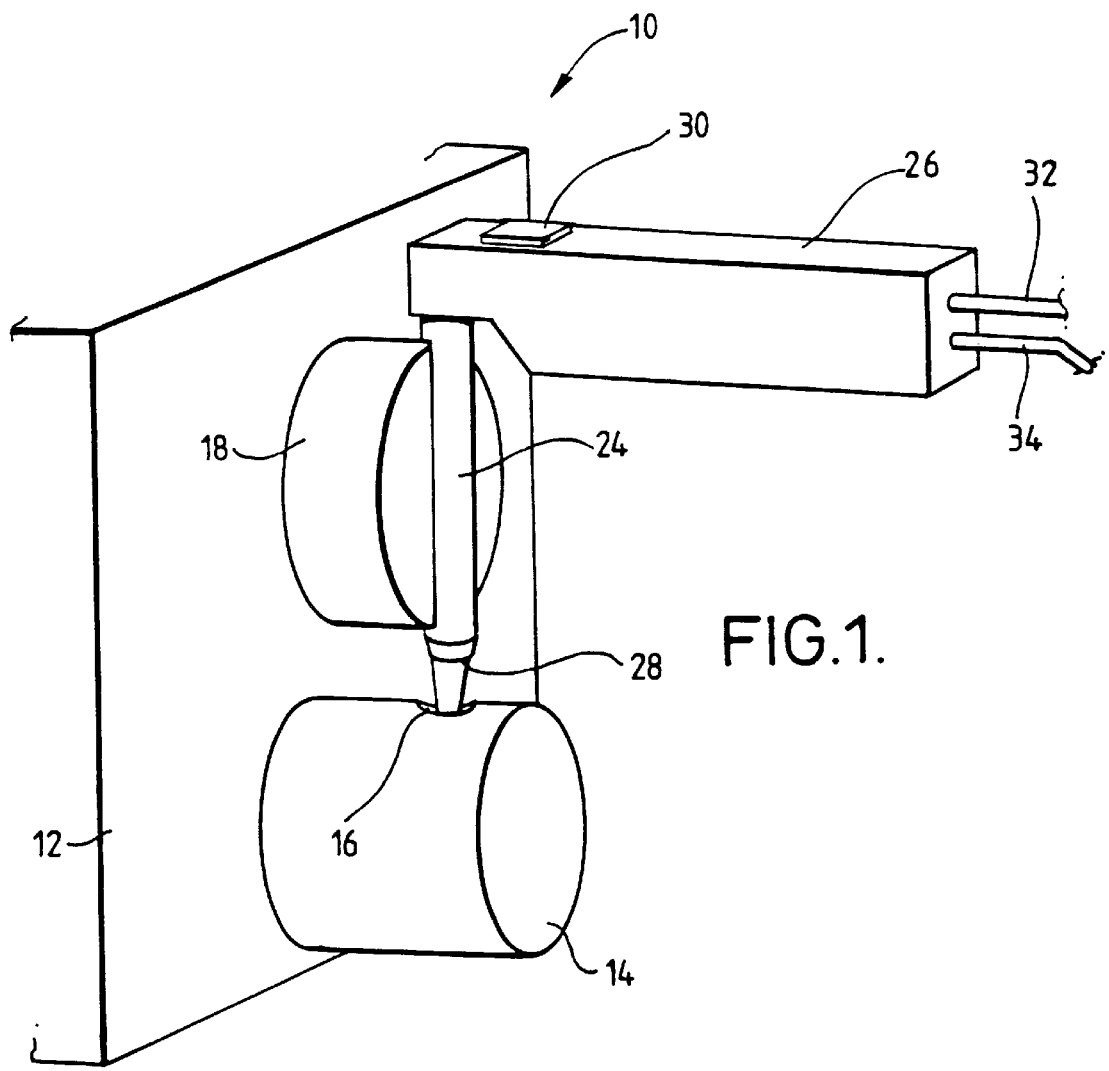
FIG. 1 is a schematic perspective view of a sample wand and a sample chamber housing forming part of the apparatus according to the invention.
Figure 2:
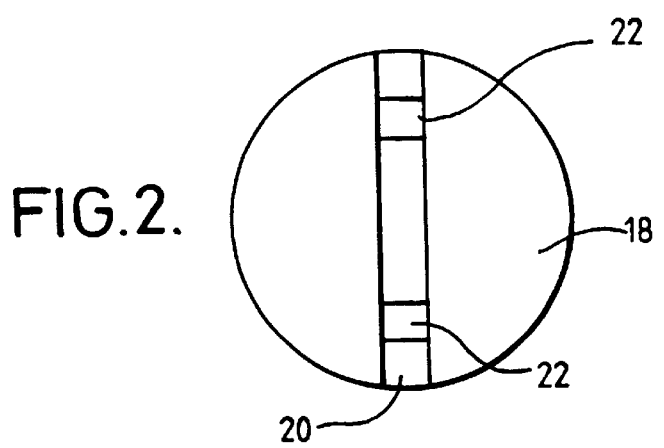
FIG. 2 is a schematic front elevation view of the sample wand alignment guide as shown in FIG. 1.
Figure 4:
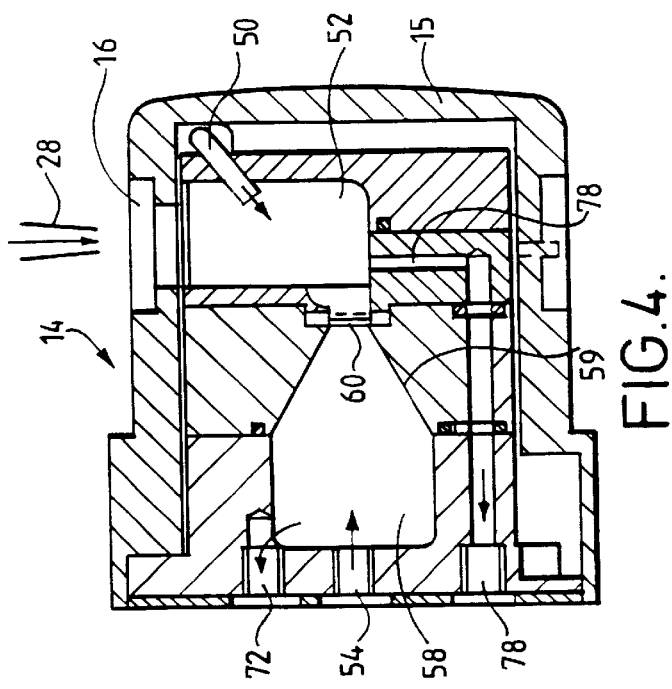
FIG. 4 is a sectional view through a sample chamber according to the invention.

Referring to FIG. 1 there is shown part of a particle sizing apparatus 10 according to the invention comprising a main housing 12 from which protrudes a sample chamber housing 14 having an inlet 16 through which a sample passes into first chamber 52 shown in FIG. 4. Additionally, a wand guide 18 protrudes from housing 12. Wand guide 18 comprises a vertical groove or channel 20 which enables alignment of nozzle 24 of hand-held wand 26 with inlet 16. Hand-held wand 26 further comprises a replaceable tip 28, a button 30, fluid inlet pipe 32 and electrical connection 34. As shown in FIG. 2 wand guide 18 comprises a pair of detectors 22 such as optical detectors to determine if wand nozzle 24 is in place within groove 20.

Figure 3:
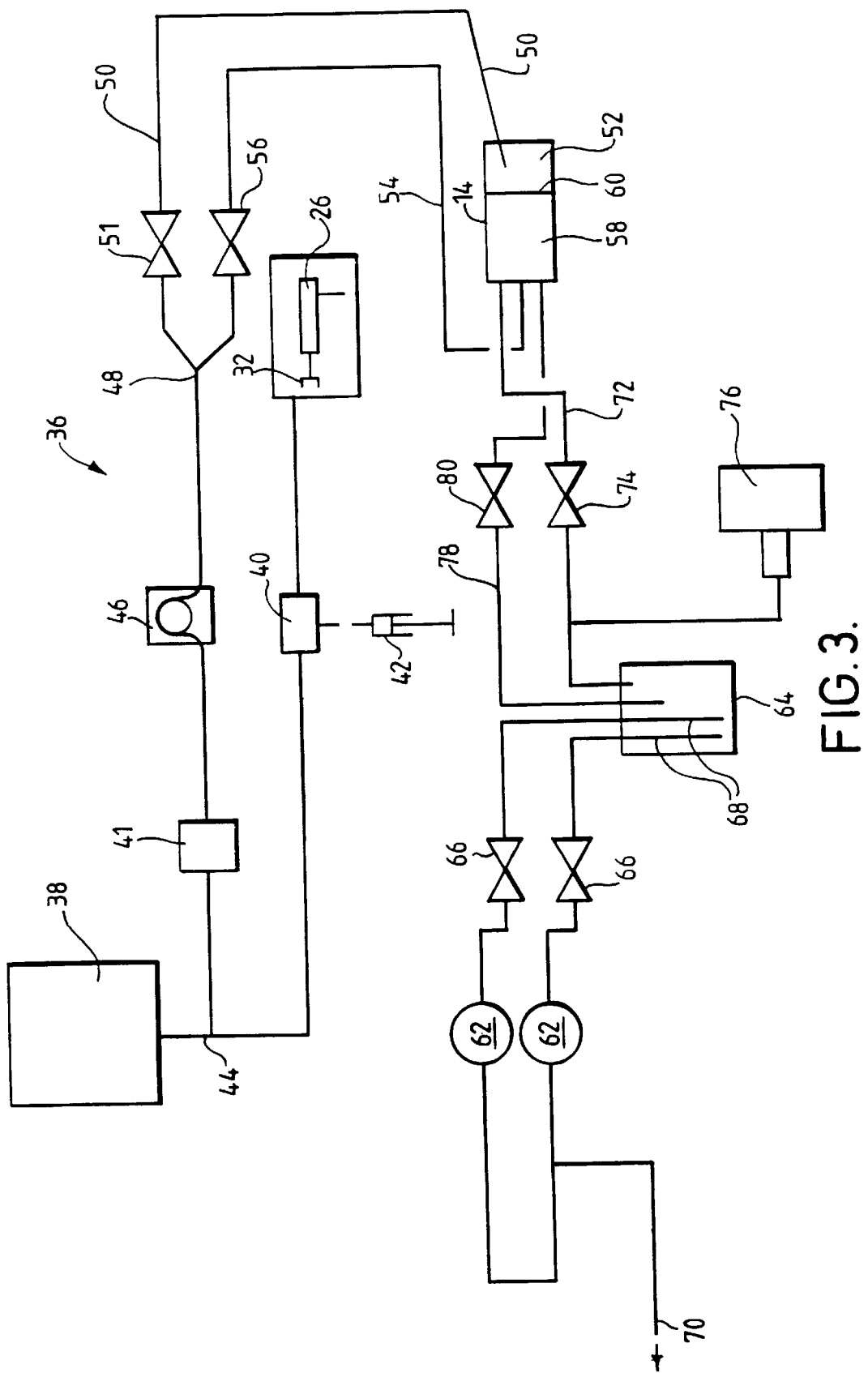
FIG. 3 is a schematic block diagram of the fluid control apparatus according to the invention.

Referring to FIG. 3 there is shown a schematic drawing of the fluid control system 36 used in apparatus 10. In fluid control system 36 a diluent reservoir 38, which can house say three liters of electrolyte for example, is connected along one path to a three-way valve 40 which is connected at one outlet to a syringe drive 42 which can comprise a 12 volt stepper motor for example, and at another outlet is connectable to wand 26 by fluid inlet pipe 32.

Reservoir 38 is also connected via a T-connector 44 to a diluent sensor 41, which can be an optical device for determining if diluent is present. A pump 46 such as a 12 volt DC peristaltic pump, drives diluent to sample chamber housing 14 via a Y-connector 48.

One outlet of Y-connector 48 is connected to tube 50 having a valve 51 such as an electrically operated pinch valve, which controls flow of diluent through tube 50 to a first chamber 52 forming part of sample chamber housing 14. The other outlet from Y-connector 48 passes through tube 54 which has a valve 56, again such as an electrically driven pinch valve, which controls flow of fluid through tube 54 into a second chamber 58 of the sample chamber housing 14. First and second chambers 52 and 58 respectively, are separated by a flow restrictor 60 having an orifice 63 (see FIGS. 7, 8 and 9). Sample chamber 14 is shown in greater detail in FIGS. 4 to 6.

System 36 further comprises a suction system comprising a pair of vacuum pumps 62.

Each pump is connected to a vacuum reservoir 64 via a valve 66, such as an electrically driven pinch valve. Purge tubes 68 pass almost to the bottom of reservoir 64 thereby to enable expulsion of any liquid in reservoir 64 via at least one of valves 66, pump 62 and outlet 70 thus for disposal.

Reservoir 64 is further connected via tube 72 to the second chamber 58 of housing 14. Tube 72 further comprises a valve 74 such as a pinch valve and a pressure transducer 76 such as a Honeywell Controls type 141PC05G device. Reservoir 64 is further connected to the first sample chamber 52 via tube 78 having a valve 80.

Figure 6:
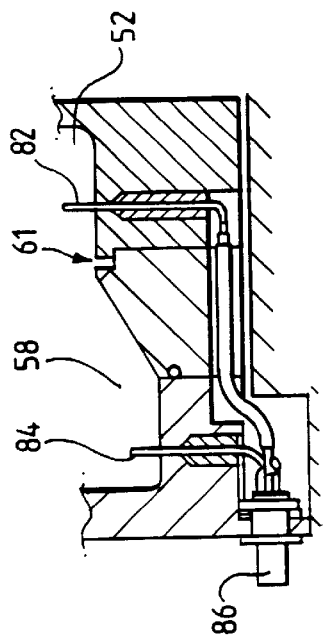
FIG. 6 is a partial sectional view of the sample chamber shown in FIGS. 4 and 5.
Figure 5:
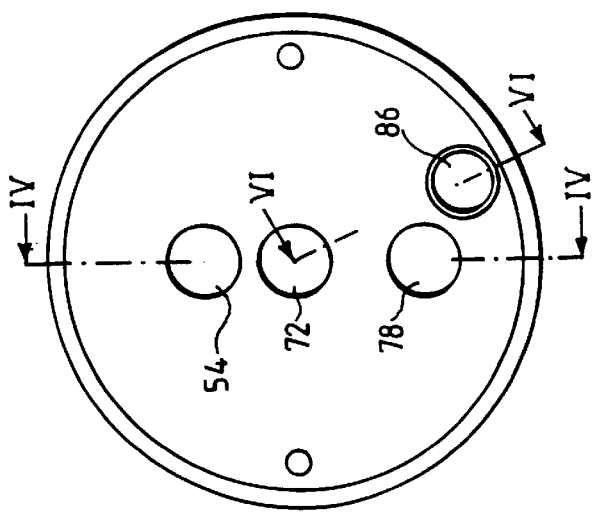
FIG. 5 is an end view from inside the apparatus of the sample chamber shown in FIG. 4.
Figure 7:
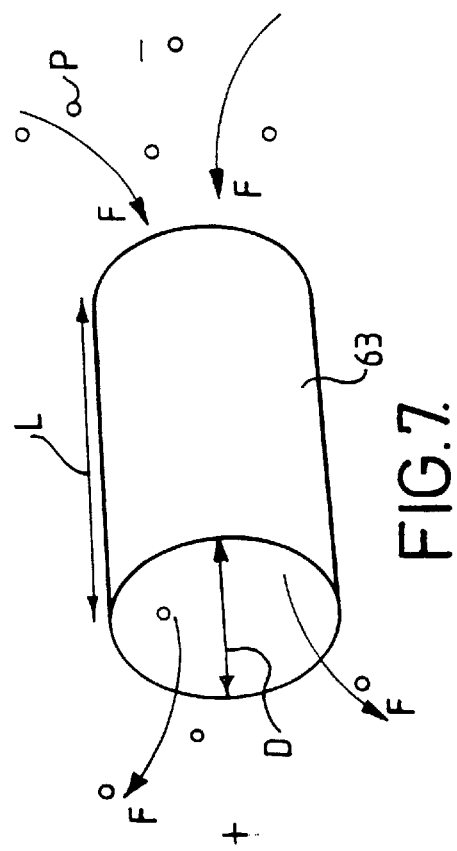
FIG. 7 is a schematic perspective view of an orifice in a flow restrictor.

Referring to FIGS. 4 to 6, sample chamber housing 14 is shown which preferably comprises an outer shield 15 against electromagnetic radiation such as a metallic casing. Inlet 16 leads to first chamber 52 which is separated from second chamber 58 by flow restrictor 60. The chambers can be made in a body of inert material such as an acrylic or other plastic. The flow restrictor can comprise a crystaline material such as ruby, sapphire, or aluminium or a polymer having a orifice 63. As shown in FIG. 7 orifice 63 has length L and diameter D, for example a length of 80 microns and diameter of 30 microns is preferred for certain sizes or volumes of particle P which during measurement flow through orifice 63 along direction F. However, other sizes of orifice are possible. Diluent tube 50 enables diluent to pass into first chamber 52 whilst tube 78 enables evacuation of the first chamber.

Similarly tube 54 allows diluent to pass into second chamber 58 and tube 72 enables the evacuation thereof. In practice the tubes can comprise different types of passageways, channels and connectors as appropriate. Inlets to sample chamber housing 14 are shown in FIG. 5.

In FIG. 6, it can be seen that a recess 61 can be provided for holding flow restrictor 60 thereby to separate chamber 52 and 58. O-rings can also be used to seal the edges of flow restrictor 60. Additionally, electrodes 82 and 84 are shown effectively on opposite sides of flow restrictor 60, i.e. one in each of chambers 52 and 58. The electrodes can be made of platinum for example and are connectable to an electronics control system via connector 86.

It has been found particularly useful to attach electrodes 84 and 82 to housing 14 using a two-part sealant and adhesive. This is in order to prevent leakage of fluid from chambers 52 and 58 and maintain the electrode in a correct position in spite of attaching and detaching chamber housing 14 from main housing 12. Preferably, the electrodes are mounted in a recess in housing 14 which can be made of acrylic or other polymer material. The upper part of the recess, that is adjacent the fluid chambers, is sealed with a water resistant and vacuum seal material such as a silicon based sealant, for example RTV silicon rubber. A second stage of adhesive is placed below the sealant to attach the electrode to the walls of the recess. A suitable adhesive is a structural acrylic adhesive. In a preferred form, chamber housing 14 is made from acrylic, the electrodes have an outer platinum coating or are made of platinum and the two-stage sealant and fixing comprises RTV silicon rubber and structural acrylic adhesive.

Preferably, chamber housing 14 is easily detachable from main housing 12. Accordingly, electrical connector 86 is preferably a simple bayonet-type connector comprising male components adapted to fit into a female socket on housing 12 for example. Additionally, as shown in FIGS. 4 and 5, tubes 72, 54 and 78 allow for easy mounting on housing 12 and can for example be the female part of a male/female connection. Accordingly, chamber housing 14 can be attached and removed from main housing 12 in a simple push/pull operation.

Referring to FIGS. 8 and 9 there is shown a second embodiment of a flow restrictor 60 according to the invention wherein orifice 63 is tapered. For example, the aperture on one side of restrictor 60 could be 32 to 38 microns in diameter whilst the orifice on the other side could be 30 microns. Accordingly, a taper of say 2 to 8 microns in the diameter of the orifice is affected across its length of say 80 microns. Preferably, the narrower orifice faces the second chamber 58 such that in use, as shown in FIG. 9a, where the restrictor 60 is made of resilient material, it flexes creating an orifice 63 having approximately parallel sides thereby enabling laminar flow through the orifice. The rest position in shown in FIG. 9b and a blow-back or clearing operation position is shown in FIG. 9c. The clearing operation is described in more detail later.

Preferably, the flow restrictor is made of a polymer such as a non-fluoride polycarbonate such as PET or polystyrene. The orifice can be laser etched into the flow restrictor.

Preferably, to assist in cleaning a blocked orifice 63, second chamber 58 comprises a tapered region 59 which narrows towards flow restrictor 60 (see FIG. 4). Additionally, preferably tube inlet 54 to chamber 58 is axially aligned with orifice 63 so that fluid passing into chamber 58 is directed to effect turbulence at flow restrictor 60 and possibly to cause reverse flow of diluent through to first chamber 52. The tapering of chamber 58 assists in this reverse flow and additionally causes circulation of diluent in chamber 58 assisting in the cleaning thereof. Further, a flexible restrictor 60 provides the enhanced clearance configuration shown in FIG. 9c.

Referring to FIG. 10 there is shown a schematic block diagram of an electronics control system 88 for the apparatus according to the invention. System 88 comprises an amplifier stage 92 for detecting and amplifying a signal from electrodes 82 and 84.

A signal power supply unit 94 is provided which generates a plus or minus voltage to be applied across electrodes 82 and 84, for example a voltage of 150 volts is preferred; across the electrodes however this can be somewhat less and can be about 30 volts. Amplifier board 92 provides an earth connection to shield 15 around sample chamber housing 14, and is additionally connected to vacuum transducer 76 and a thermocouple or temperature probe 95 such as a National Semi-Conductor type LM35CAH device which can be located for measurement of the diluent temperature in second chamber 58.

An amplified sample signal is communicated to a 3½ digit variable potentiometer 96 along line 98 from amplifier stage 92. The potentiometer forms part of an attenuator board 100 which enables adjustment of the signal gain as necessary for the selected orifice size and application. The output from the attenuator board 100 is fed to a 14 bit analogue to digital converter on measurement board 102. The electrode current, vacuum signal and temperature signal are fed along lines 104, 106 and 108 respectively from amplifier board 92 to an 8 bit analogue to digital converter on measurement board 102. Measurement board 102 comprises a channel of 500 kHz or 1 MHZ conversions at 14 bits, local storage for a channel of 14 bit data, eight channels of 8 bit (slow) A-D conversion at 100 microsecond conversion, controlling status registers for these devices, 16 bits of digital output control and 16 bits of digital input control.

Lines 110 and 112 are provided between measurement board 102 and amplifier board 92 respectively to enable reversing of the voltage polarity across the electrodes 82 and 84 and also for commencing and stopping an electrode calibration sequence to be described later.

A series of digital input/output ports are provided from measurement board 102. These are connected at lines 114 to 120 a stepper motor driver 43 which is in turn connected to syringe stepper motor 42. Line 114 carries an opto signal from the syringe drive indicating that the syringe is in its home position. Clock, enable and direction signals are relayed to stepper driver 43 via lines 116, 118 and 120 respectively.

The other input/output ports on measurement board 102 communicate with driver board 122. This board, for example, controls the opening and closing of valves 51, 56, 66, 74 and 80. It also controls the diluent pump 46 and vacuum pumps 62. The diluent sensor 41 and user wand button 30 are also connected to driver board 122.

A power supply unit 90 provides requisite voltage to drive the system 88. Also, a programmable device such as a computer 103 is provided to drive and communicate with boards 100 and 102 (or other elements as necessary). A peripheral device such as a display and/or printer 124 is also provided.

Figure 11A:
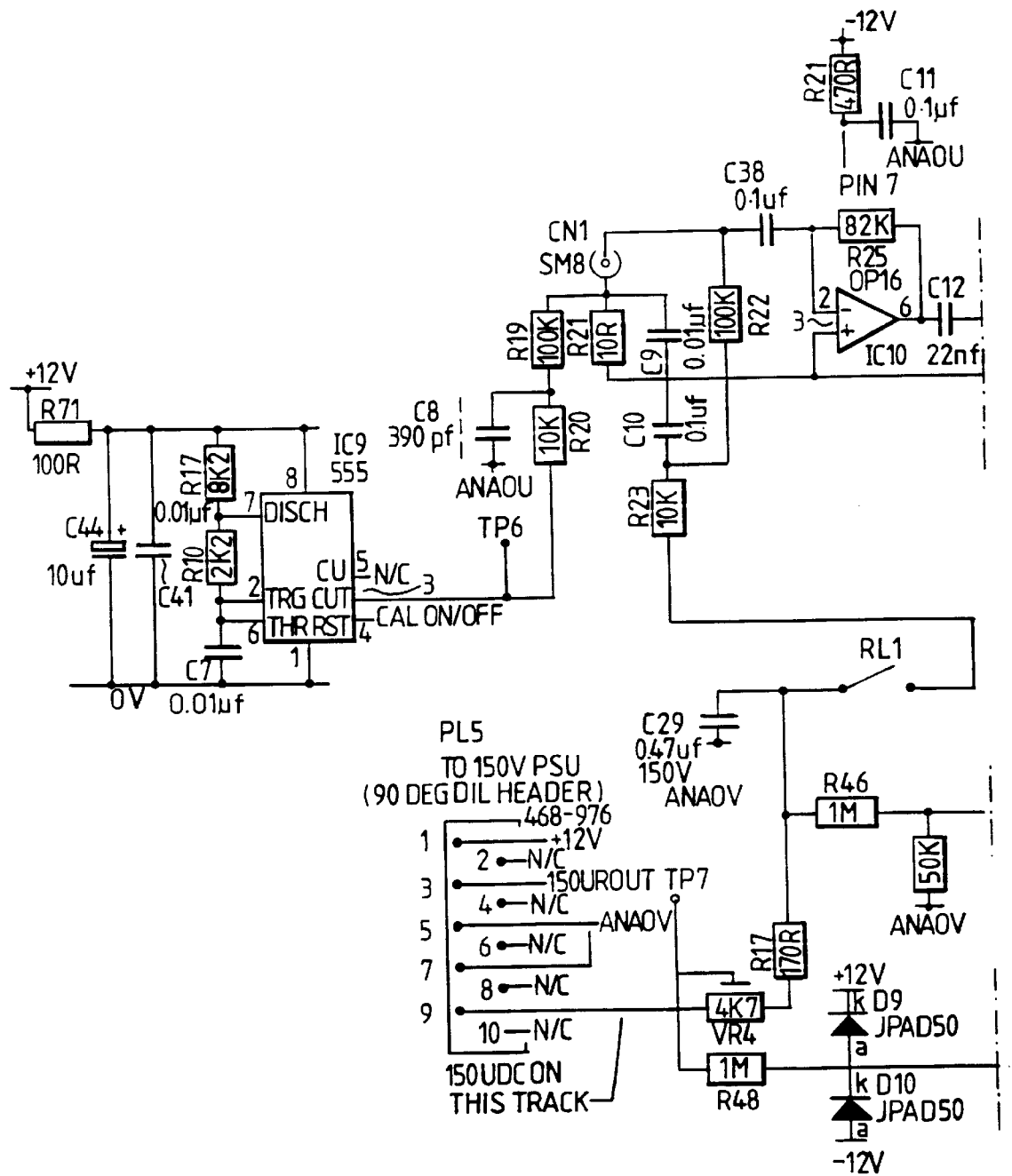

Referring to FIGS. 11a and 11b there is shown a circuit diagram for part of the amplifier board 92. A particle signal amplification path comprises four low noise op-amps IC10, IC11, IC12 and IC13 having frequency selective components which allow bandpass filtration of the signal to remove DC and high frequency noise. Amplifier IC11 has a gain adjustment potentiometer that can be set during manufacture and sealed. Amplifier IC13 provides amplifier board 92 with a DC offset adjustment (say −3.2V) using the resistor and potentiometer network R35, R36, VR3 and R37. An electrode (82 or 84) is connected at CN1 and is AC coupled to op-amp IC10 via capacitor C38. A signal generating voltage source 94 of say 150 volts in this example, connects to the signal path at PL5 and is controlled by reed relay RL1. Resistors R23 and R22 form a high impedance path in comparison to the diluent electrolyte through the orifice making the source 94 appear as a constant current generator.

The amplified signal output at CN2 passes along line 98 to attenuator board 100 shown in FIG. 10. An orifice current signal can be derived from DC current flowing through the chain VR4, RL1, R23, R22, R21, R47 and orifice 63 via CN1. The electrode voltage source 94 connects at PL5 and a voltage proportional to the orifice current is expressed across VR4 and R47 and amplified by IC14a. This is further conditioned at amplifier IC14b and output to measurement board 102 via line 104 shown in FIG. 10.

The operation of the system is as follows. The system is formally calibrated for a given electrode voltage, orifice diameter and diluent using inorganic machined particles of known size or volume. After calibration at manufacture, a further calibration verification can be conducted during use of the system as described later. Both first and second chambers 52 and 58 of the sample chamber 14 are washed by alternately opening valve 51 and 56, and valves 80 and 74 respectively, and pumping diluent using pump 46. For example, chambers 52 and 58 can be filled and emptied using the vacuum system including pump 62 and tube 72 and 78, for example a series of three times before again filling chamber 62 and 58 to enable an electrical calibration test. A series of calibration pulses is applied to one of the electrodes 82 or 84 at CN1 using 1C9 shown in FIG. 11 such as a CMOS 555 timer device. The output voltage at CN1 can be controlled for example at 12 volt peak to peak thereby to enable an impedance measurement across the orifice which signal might for example be in the order of 1 millivolt for a nominal 30 micron orifice. The pulse width can be in the order of 20 to 40 microseconds for frequencies in the order of 15 to 20 kHz. The mean pulse height and number of pulses are monitored as part of the calibration verification, a total of three repeated calibration measurements can be attempted before the sequence is aborted and an error condition signal provided to the user for example at a VDU display or similar output device 124 connected to board 102. The fluid content of the diluent reservoir 38 is then checked for example using a sensor 41 connected to board 122 shown in FIG. 10.

Syringe 42 is then loaded by directing the three way valve 40 to relay fluid from reservoir 38 into syringe 42 and driving stepper motor 43 a calibrated number of steps in order to load the syringe unit with a known volume of diluent such as 1 milliliter. The user is then requested to place a disposable sterilised tip 28 on the end of nozzle 24 of wand 26 and press the button 30 to confirm. The user then places the disposable tip in the sample fluid and again operates button 30 and syringe 42 is driven down a pre-programmed amount thereby to draw sample fluid into the disposable tip 28.

The user places the sample wand so that nozzle 24 is aligned in groove 20 and tip 28 protrudes into first chamber 52. First chamber 52 is emptied by opening valve 80 and using pump 62. The operator presses button 30 to initiate a dispense sequence wherein syringe 42 is driven with valve 40 directing fluid through pipe 32 such that the sample and diluent are emitted from wand 26 into first chamber 52. If during this operation, detectors 22 determine that nozzle 24 is not in position or has moved away from this position in channel 20, the system waits for the nozzle to be correctly re-positioned. If the sample aspiration, dilution and presentation to chamber 52 is not completed in a predetermined interval, eg 2 minutes, the measurement is aborted and the sample chamber cleaned and the process re-initiated.

It will be appreciated that it is possible by determining the extent of movement of syringe 42 in any direction to quantify, using stepper motor 43, the amount of sample drawn up through tip 28 and the amount of diluent drawn in to syringe 42 to be mixed therewith, and hence the concentration of sample and diluent can be accurately determined.

Second chamber 58 is primed with fresh diluent through tube 54 by opening valve 56 and operating pump 46 to ensure that it is substantially full. The amount of diluent should be sufficient to enable an electrically conductive path between electrodes 82 and 84 across the flow restrictor 60. Preferably an initial priming of second chamber 58 is conducted by passing diluent through tube 54, as previously described, causing turbulence in chamber 58. This acts to reduce the possibility of blockage of orifice 63.

The vacuum reservoir 64 is evacuated of fluid using pumps 62 such that when valve 80 and 74 close a vacuum in the order of 130 mm Hg is established in reservoir 64 as read by transducer 76. For example, one of pumps 62 can be turned off or the associated valve 66 closed, on reaching 90% of the predetermined vacuum pressure and using only one of pump 62 to achieve the predetermined level of vacuum.

Valve 74 is opened with valve 56 closed and accordingly some sample and diluent is drawn through the orifice 63 of flow restrictor 61, that is between chambers 52 and 58. The known voltage is applied to the electrode 82 (or 84). After a stabilising delay of say 2 seconds, the current through the orifice, i.e. between electrodes 82 and 84 is checked at line 104 (see FIG. 10). The current start value or initial value is stored for use in later comparative checks.

Preferably the large DC voltage is removed and a calibrator reference signal applied to electrode 82 (or 84) as previously described.

Figure 12:
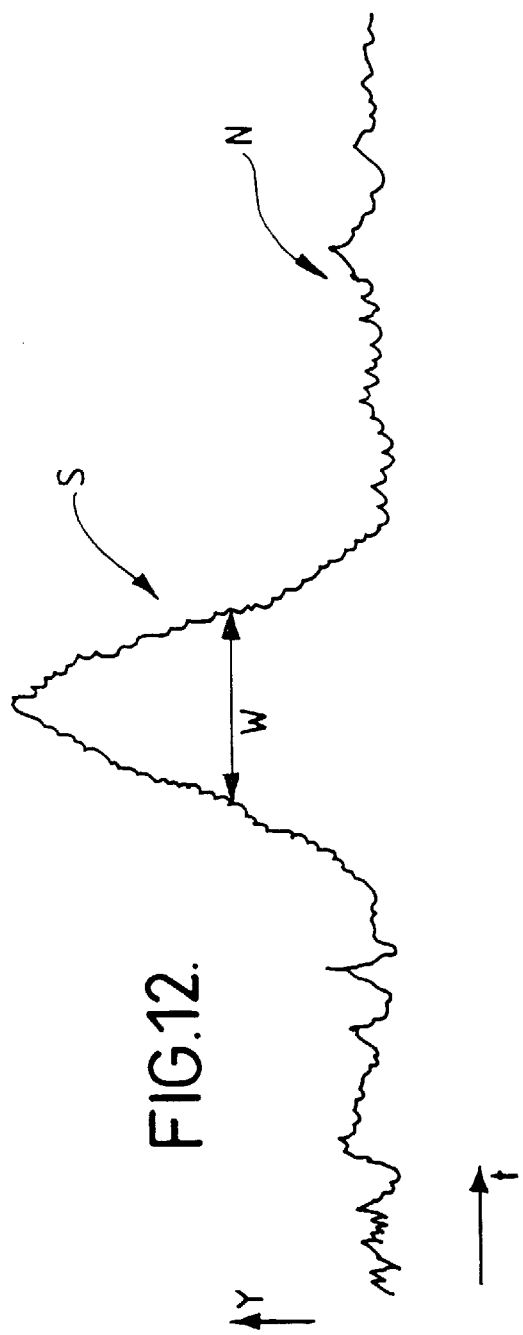
FIG. 12 is a schematic view of a signal pulse detected and analysed by the apparatus according to the invention.

The known DC voltage, is applied to electrode 82 and the resulting signal amplified between CN1 and CN2 of FIG. 11 and output from the amplifier board 92 at line 98 is shown in FIG. 8. An example of the type of pulse observed when a particle passes through orifice 63, is shown in FIG. 12. The pulse signal S has a height, or voltage, determined by the volume of the particle. The width W of the pulse is determined by the time for the particle to flow through the orifice, i.e. the flow rate and axial length L of the orifice. The signal also has a characteristic background noise N.

In one example of the operation of the system, the programmable device 103 sends a signal to measurement board 102 to initiate 14 bit data conversion at 16384 conversions every two microseconds each. The gain on the attenuator board 100 can then be adjusted as necessary to bring the signal within a suitable range. When the data is captured, it can be sent from measurement board 102 to be stored for example in computer RAM forming part of device 103. The signal such as shown in FIG. 10 is analysed by, for example, applying a smoothing algorithm to the raw data to remove high frequency noise.

Within a given set or batch of captured data, the system detects a pulse signal S by an increasing leading edge over time. A minimum number of positive going sample values are required to trigger the search for a corresponding negative going edge thereby to detect a pulse signal S. A potential pulse is rejected if a minimum number of negative going samples is not detected after passing through a peak position. The system measures the width of the signal as the point half way along the leading edge to a point on a trailing edge where the voltage becomes less than the starting point on the leading edge. Knowing the expected particle flow rates, it is possible to detect falling fluid flow through the orifice by an increasing pulse width. This can be indicative of a partial blockage of orifice 63. However, if the pulse width is too narrow, this data is rejected as noise rather than a signal. The pulse height of the signal S can be measured between a net baseline level in the noise N, adjacent signal S and mean or average, peak value of the signal S. As an alternative, the peak height can be determined simply from the value at the first positive going point in a detected pulse signals and taking the difference between this value and that at the pulse maximum. The pulse area is calculated by integration of signal S and is stored both for a batch and an accumulative histogram for the sample.

Occasionally, two particles pass through orifice 63 at the same time. This can result in a single pulse representative of the volume of both particles, however, sometimes both pulses are resolvable from one another since a first peak is observed followed by a negative going pulse which does not reach the base line voltage before a second positive going pulse due to the second particle occurs. These incidences can be referred to as primary and secondary coincidence respectively. Preferably, the sample concentration of say a million particles per ml is such that these coincidences very rarely occur, however, pulses from secondary coincidence can still be analysed and form part of the data by extrapolating along the negative going edge of the first pulse to determine a pulse width and also by extrapolating the positive going edge of the second pulse also to determine a pulse width. The initial value at the leading edge of the first pulse can be used in the determination of the height of the second pulse.

For each signal detected in a batch the pulse width and pulse height are stored and added to data for that batch. If it is determined that the batch of data is good, checks carried out are described later, the batch data is added to a cumulative pulse height histogram, which is indicative of the particle volume distribution for the sample, and the cumulative pulse width histogram. In this example each batch of data represents the signals over 32 ms of data capture. Also the number of pulses detected is stored as a current batch value and total for all batches for a given sample (i.e. series of measurements). A further store of noise can also be conducted of say any region of noise not containing a pulse signal S for a given a set of captured data. A current value derived from that before and after the batch of data is stored as a mean value of the two measurements. The current value is output at PCRT of the circuit shown in FIG. 9, or line 104 of amplifier board 92 shown in FIG. 10. The level of vacuum in reservoir 76 is also measured for each batch. Batch data is added to overall sample data to provide cumulative sample histograms.

Typically, measurements of a sample are made over a twenty to thirty second time period during which the sample is caused to flow through orifice 63, preferably a particle at a time. The flow can be maintained by repeated evacuation of vacuum reservoir 64 using pump 62 so as to retain an under pressure in the reservoir which draws sample from chamber 52 through to chamber 58, ie. due to the over pressure of atmospheric pressure at inlet 16 to chamber 52. For example, three successive evacuations of chamber 64 to a preset pressure might be necessary in a thirty second measurement period, depending on how often a deblocking sequence, described later, is conducted.

Under block conditions, the impedance between electrodes 82 and 84 varies significantly and this affects the gain, of what could be considered the orifice 63, or amplifier stage IC10 and so on. Under these conditions, a pulse signal S can approach that of a square wave. This can be monitored by analysing a detected pulse signal S from the time difference between the signal increasing through two distinct and predetermined voltage thresholds above the DC off-set level, and the time for the signal to return back through the two predetermined voltage levels. If the time difference between passing through the lower levels and the upper levels is substantially equal and non-zero then it is indicative of a block having occurred at orifice 63. Additionally, where a square wave signal is followed by a recovery curve which has a characteristic recovery rate determined by the electronic circuitry and which is positive going, in the sense of signal S shown in FIG. 12, then this signal is indicative of a very large particle in the vicinity of orifice 63. The pulse is designated a rejected pulse.

The background noise N is also monitored. By analysing the frequency domain of the noise, following Fourier transformation, it is possible to detect a partial block since the gain of the amplifier is affected and anomalous frequency amplification can be seen. If a factor of say two difference in amplitude is seen in any frequency component then the data can be rejected. Accordingly, the comparison between background noise and an average background noise can indicate partial or complete blockage of orifice 63.

To check if a given batch of data is acceptable, a first check can be the number pulses observed in the period of the data capture. If the number of pules vary significantly in comparison to the mean number of pulses per batch, say by greater than or less than 50%, or alternatively one standard deviation from the mean, the data can be rejected. Also, comparison of the mean current value at the start and finish of batch data capture with the start current value can be made. If the difference is greater than say +/−20% then the batch data can be rejected. Additionally, the mean current value compared to the mean current value for the previous batch of data can be checked. If the difference is more than say an increase of 10% or a decrease of 5%, then the second batch data can be rejected. Additionally, comparison of the noise with static limits can be made. For example, using the Fourier analysis if a given frequency component varies by a factor of two in comparison with the mean, then this can be taken as defective data. Comparison of the mean pulse width for a batch of data with the cumulative mean pulse width can be made. If the discrepancy is greater than say 10% then the batch of data can be rejected assuming that a significant number of pulses is detected per batch, say at least 30 and preferably 100 pulses per batch. Additionally, the number of rejected pulses, or square wave pulses is monitored, data can be rejected when observing either one or more rejected pulses in a given batch. In the event of any of these events occurring which leads to data rejection, a deblock sequence is preferably initiated.

Preferably, the deblock sequence is initiated by turning off the DC voltage on electrode 82 and applying a pulse sequence which can be the calibration pulse sequence. Accordingly, an ultrasonic vibration, in the frequency range 15 to 20 kHz, is set up within the electrolyte. Chamber 58 is also primed by operating pump 46, opening valve 56, whilst valve 74 is also open. The priming sequence is terminated after a short time period of say 100 milliseconds, and the calibration or ultrasonic pulses are also turned off. The large DC voltage is reapplied to electrode 84 and a time delay of say one second is allowed to elapse to stabilize fluid flow. The data measurement sequence is then recommenced as the measurement board is re-initiated, again the attenuator board is adjusted and an initial current value recorded.

Preferably, the data received immediately preceding a deblock sequence is subtracted from cumulative data and rejected as being inconsistent.

The measurement sequence is repeated until the required quantity of fluid has passed through the orifice. This is determined knowing the size of orifice 63, the flow rate from pulse widths and the duration of measurement. Measurement of a sample can also be stopped when the required number of particles within a set range has been measured, or a fatal error occurs and is not rectified such as the orifice current changing and not returning to the value of the start current, the diluent reservoir becoming empty, the data repetition becoming inconsistent, or the base line noise level rising above an acceptable static level.

Upon completion of a measurement sequence, the sample is evacuated from chamber 52 by opening the valve 80. The sample side of the chamber 52, can then be cleaned through a number of rinse cycles by opening valve 51 and pumping at pump 46.

Preferably, an intelligent washing sequence is performed whereby the concentration of sample particles from a previous sample is monitored i.e. from the number of particle signals detected in a known measurement volume. The apparatus can be calibrated to determine how many rinses are required to clean the chambers following a given concentration of sample.

I claim:

1. A sample chamber housing for particle sizing apparatus comprising a first sample chamber for holding a liquid sample and a second chamber for holding a liquid, a liquid communication passage between the first and second chambers adapted to receive a flow restrictor comprising a single aperture for sizing particles, wherein the liquid sample flows from the first chamber to the second chamber through the single aperture, an inlet aperture open to ambient atmospheric pressure for passing the sample into the first sample chamber, an outlet from the first chamber enabling automatic removal of the sample therefrom, and a second inlet into the second chamber for injecting cleaning fluid into the second chamber, the second inlet being disposed to direct the cleaning fluid directly at the flow restrictor in use and to cause a reverse flow of the cleaning fluid to the first chamber.

2. A sample chamber housing according to claim 1 wherein the second chamber tapers towards the liquid communication passage between the first and second chambers thereby to guide liquid towards the restrictor in use.

3. A sample chamber housing according to claim 1 comprising a liquid outlet from the second chamber for automatic removal of liquid therefrom.

4. A sample chamber housing according to claim 1 wherein the first chamber and the second chamber comprise substantially smooth surfaces to encourage removal of liquid therefrom.

5. A sample chamber housing according to claim 1, further comprising a third inlet in the first chamber which said third inlet is disposed to direct liquid at the restrictor in use.

6. Particle sizing apparatus comprising a sample chamber housing according to claim 1 and further comprising a first and a second electrode disposed in the first and second chambers respectively.

7. A particle sizing apparatus according to claim 6 further comprising a third inlet to the first chamber which third inlet is disposed to direct liquid at the restrictor in use.

8. Apparatus according to claim 6 comprising fluid flow control means which comprises fluid communication to a reservoir of one of diluent and cleaning liquid.

9. Apparatus according to claim 6 having a fluid removal control means which comprises a vacuum pump for removal of liquid from at least one of the first and second chambers.

10. Apparatus according to claim 6 comprising means for effecting a pressure differential between the first and second chambers.

11. Particle sizing apparatus according to claim 6 further comprising a liquid outlet from the second chamber and means for controlling removal of liquid through the liquid outlet from the second chamber.

12. Particle sizing apparatus according to claim 6 comprising a wand, means for drawing liquid into the wand and means for expelling liquid from the wand into the first sample chamber.

13. Particle sizing apparatus according to claim 12 wherein the means for drawing and expelling liquid comprises a pump and valve arrangement.

14. Particle sizing apparatus according to claim 13 wherein the pump comprises a controlled metering device.

15. Particle sizing apparatus according to claim 13, wherein the valve arrangement comprises a three-way valve having three openings enabling fluid to be expelled along two openings from the valve.

16. Particle sizing apparatus according to claim 13 further comprising means for ensuring that the wand is correctly positioned for inserting the liquid sample into the first sample chamber.

17. Apparatus according to claim 14 wherein the controlled metering device comprises a syringe driven by a stepper-motor.

* * * * *